US005604226A

United States Patent [19]

Kagawa et al.

[11] Patent Number: 5,604,226

[45] Date of Patent: Feb. 18, 1997

[54] PYRIDAZINONE DERIVATIVES, PROCESSES FOR PRODUCTION THEREOF AND USE THEREOF

[75] Inventors: Takashi Kagawa, Hashimoto; Takuya Motokawa, Sakai; Masanori Yoshida, Hashimoto; Yoshitami Oshita, Kawachinagano; Kazuo Kanai, Sakai, all of Japan

[73] Assignee: Nihon Nohyaku Co., Ltd., Tokyo, Japan

[21] Appl. No.: 356,510

[22] Filed: Dec. 15, 1994

[30] Foreign Application Priority Data

Dec. 16, 1993 [JP] Japan .................................. 5-343405

[51] Int. Cl.$^6$ .................................. C07D 237/16

[52] U.S. Cl. .......................... 514/247; 544/240; 544/241

[58] Field of Search .................................. 544/240, 241; 514/247

[56] References Cited

U.S. PATENT DOCUMENTS 4,978,665 12/1990 Tanikawa et al. ...................... 544/241
5,011,839 4/1991 Tanikawa et al. ...................... 514/247
5,314,883 5/1994 Tanikawa et al. ...................... 514/252

FOREIGN PATENT DOCUMENTS 0482208 4/1992 European Pat. Off. .
5-112454 5/1993 Japan .

*Primary Examiner*—Donald G. Daus
*Attorney, Agent, or Firm*—Cushman Darby & Cushman IP Group of Pillsbury Madison & Sutro LLP

[57] ABSTRACT

Pyridazinone derivatives of formula (I):

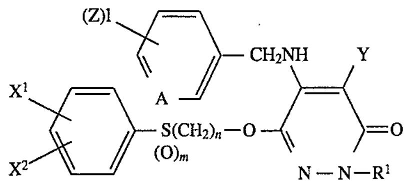

(I)

wherein $R^1$ represents a hydrogen atom or a methyl group which may be substituted with an aliphatic cyclic amino group optionally containing a hetero atom in the ring thereof; each of $X^1$ and $X^2$ independently represents a hydrogen atom, a halogen atom, an alkyl group having 1 to 6 carbon atoms, an alkoxy group having 1 to 6 carbon atoms, a cyano group, a nitro group or a group shown by —CO—$NR^2R^3$ (wherein each of $R^2$ and $R^3$ independently represents an alkyl group having 1 to 6 carbon atoms); Y represents a halogen atom; Z represents an alkoxy group having 1 to 6 carbon atoms; l represents 0 or an integer of 1 to 3; A represents CH or N; m represents 0 or an integer of 1 or 2; and n represents an integer of 1 to 8, exhibit a platelet aggregation inhibiting activity and are useful for the treatment of circulatory disorders such as cerebral infarction.

6 Claims, No Drawings

PYRIDAZINONE DERIVATIVES, PROCESSES FOR PRODUCTION THEREOF AND USE THEREOF

BACKGROUND OF THE INVENTION

1. Field of the Invention

The present invention relates to pyridazinone derivatives or pharmacologically acceptable salts thereof which exhibit an inhibitory activity against platelet aggregation and are thus useful for the treatment of circulatory disorders such as cerebral infarction or myocardial infarction.

2. Related Art

In recent years, thrombosis has been considered to be a major cause for circulatory disorders such as cerebral infarction or myocardial infarction. For the prevention and treatment of such disorders, a treatment has been widely spread in the clinical field, using plate aggregation inhibitors which lower the function of platelet. However, the history is relatively new and it has been expected to develop excellent drugs of this category.

It is shown in Japanese Patent Application KOKAI (Laid-Open) Nos. 63-30187 and 2-256668, European Patent Disclosure Nos. 0275997 and 0376079, and U.S. Pat. Nos. 4,978,665 and 5,011,839 that pyridazinone derivatives show a strongly antagonistic activity against SRS-A (slow reacting substance of anaphylaxis). However, these prior publications are silent on a platelet aggregation inhibiting activity. Compounds shown in Japanese Patent Application KOKAI No. 5-112454 and International Patent Application KOKAI No. W091/16314 are already known as platelet aggregation inhibitors but the effect is not satisfactory.

SUMMARY OF THE INVENTION

Under the circumstances, the present inventors have synthesized novel pyridazinone derivatives and made extensive investigations on their pharmacological activity. As a result, it has been found that pyridazinone derivatives represented by general formula (I):

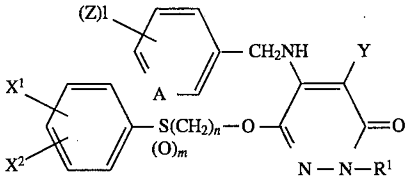

(I)

wherein $R^1$ represents a hydrogen atom or a methyl group which may be substituted with an aliphatic cyclic amino group optionally containing a hetero atom in the ring thereof; each of $X^1$ and $X^2$ independently represents a hydrogen atom, a halogen atom, an alkyl group having 1 to 6 carbon atoms, an alkoxy group having 1 to 6 carbon atoms, a cyano group, a nitro group or a group shown by —CO—$NR^2R^3$ (wherein each of $R^2$ and $R^3$ independently represents an alkyl group having 1 to 6 carbon atoms); Y represents a halogen atom; Z represents an alkoxy group having 1 to 6 carbon atoms; l represents 0 or an integer of 1 to 3; A represents CH or N; m represents 0 or an integer of 1 or 2; and n represents an integer of 1 to 8, exhibit an excellent platelet aggregation inhibiting action. The present invention has thus been accomplished.

A first aspect of the present invention is thus to provide the pyridazinone derivatives of general formula (I).

A second aspect of the present invention is to provide processes for producing the pyridazinone derivatives of general formula (I).

A third aspect of the present invention is to provide platelet aggregation inhibitors comprising the pyridazinone derivatives of general formula (I) as an effective ingredient.

DETAILED DESCRIPTION OF THE INVENTION

In the general formula (I) described above, examples of the alkyl group having 1 to 6 carbon atoms include methyl, ethyl, isopropyl, n-propyl, n-butyl, i-butyl, s-butyl, n-pentyl and n-hexyl; examples of the alkoxy group having 1 to 6 carbon atoms include methoxy, ethoxy, n-propoxy, n-butoxy, i-butoxy, s-butoxy, n-pentyloxy and n-hexyloxy; and examples of the halogen atom include fluorine, chlorine, bromine and iodine.

Preferable examples of the compounds of the present invention are 4-bromo-5-(3,4-dimethoxyphenyl-methylamino)-6-[2-(4-chlorophenylthio)ethyloxy]-3(2H)-pyridazinone, 4-bromo-5-(3,4-dimethoxyphenylmethylamino)-6-[2-(4-fluorophenylsulfinyl)ethyloxy]-3(2H)-pyridazinone, 4-bromo-5-(3,4-dimethoxyphenylmethylamino)-6-[2-(2,4-dimethylphenylsulfonyl)ethyloxy]-3(2H)-pyridazinone, 4-bromo-5-(3,4-dimethoxyphenylmethylamino)-6-[2-(2,4-dimethylphenylsulfinyl)ethyloxy]-3(2H)pyridazinone, 4-bromo-5-(3,4-dimethoxyphenylmethyl-amino)-6-[2-(phenylthio)ethyloxy]-3(2H)-pyridazinone, 4-bromo-5-(3,4-dimethoxyphenylmethylamino)-6-[2-(4fluorophenylthio)ethyloxy]-3(2H)-pyridazinone.

Particularly preferable examples of the compounds of the present invention are 4-bromo-5-(3,4-dimethoxyphenylmethylamino)-6-[2-(phenylsulfinyl)ethyloxy]-3(2H)-pyridazinone, 4-bromo-5-(3,4-dimethoxyphenylmethylamino)-6-[2-(4-methylphenylsulfinyl)ethyloxy]-3(2H)-pyridazinone, 4-bromo-5-(3,4-dimethoxyphenylmethylamino)-6-[2-(2-chlorophenylsulfinyl)ethyloxy]-3(2H)-pyridazinone, 4-bromo-5-(3,4-dimethoxyphenylmethylamino)-6-[2-(2-fluorophenylsulfonyl)ethyloxy]-3(2H)-pyridazinone, 4-bromo-5-(3,4-dimethoxyphenylmethylamino)-6-[2-(2,4-dimethylphenylthio)ethyloxy]-3(2H)-pyridazinone.

The compounds of the present invention which are represented by general formula (I) may be employed as platelet aggregation inhibitors, as they are or in the form of acid addition salts thereof. In the case of the salts, there are used inorganic acids such as hydrochloric acid, sulfuric acid, nitric acid, etc. and organic acids such as oxalic acid, methanesulfonic acid, etc.

The compounds represented by general formula (I) may be prepared, e.g., by the following process:

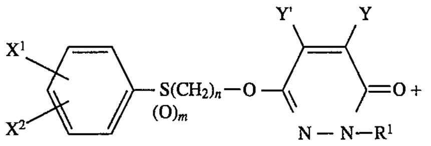

(II)

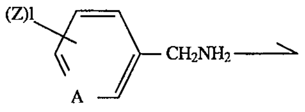

(V)

-continued

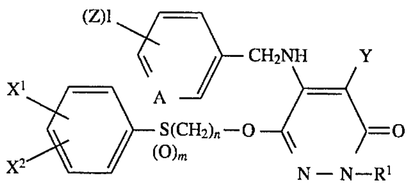

(I)

wherein $R^1$, $X^1$, $X^2$, Y, Z, A, l, m and n have the same significance as defined above and Y' represents a halogen atom.

The compounds of formula (I) wherein m is 1 or 2 may also be prepared by the following process.

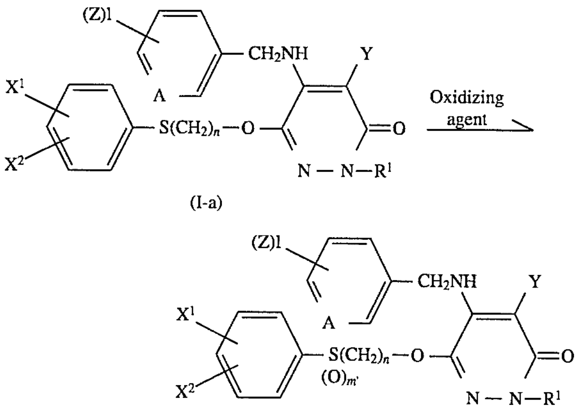

(I-a)

(I-b)

wherein $R^1$, $X^1$, $X^2$, Y, Z, A, l and n have the same significance as defined above and m' represents an integer of 1 or 2.

1) Preparation of Compound (I):

The compound shown by general formula (II) is reacted with the compound represented by general formula (V) at a temperature of 50° C. to 150° C. for 3 to 24 hours, in a solvent such as tetrahydrofuran, dioxane, dimethylformamide, dimethylacetamide, acetonitrile, N-methylpyrrolidone or water, or a solvent mixture thereof, in the presence of an equimolar amount or excess of an alkaline metal salt such as sodium hydrogencarbonate or sodium carbonate, an organic base such as triethylamine, diisopropylethylamine, pyridine, 4-dimethylaminopyridine, diazabicycloundecene, etc. Thus, the compound represented by general formula (I) can be obtained. The reaction proceeds in an equimolar amount of the reactants so that the compound shown by general formula (V) may be used in an equimolar amount based on the compound shown by general formula (II). However, the compound of formula (V) may also be used in an excess amount. Where the compound of formula (V) is employed also as a base, at least 2-fold amount of the compound (V) is used.

2) Preparation of Compound (I-b):

The compound of general formula (I-b) may be prepared by reacting the compound represented by general formula (I-a) with 1 to 3 mols of an oxidizing agent such as hydrogen peroxide, peracetic acid, metachloroperbenzoic acid, performic acid, potassium permanganate, chromic acid, potassium dichromate, etc., at a temperature of 0° C. to 150° C. for 1 to 24 hours in a solvent such as water, acetic acid, formic acid, dichloromethane, chloroform, ether, benzene, etc.

3) Preparation of Compound (I-c):

The compound of general formula (I) wherein $R^1$ represents a methyl group substituted with an aliphatic cyclic amino group optionally containing a hetero atom in the ring thereof may also be prepared, e.g., by the following process:

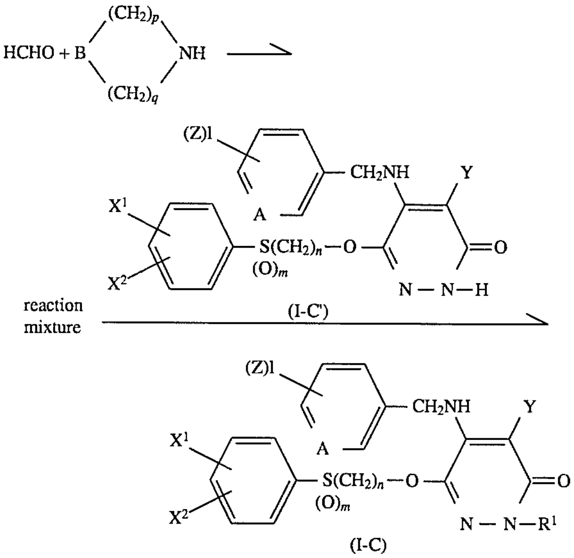

(I-C')

(I-C)

wherein $R^1$, $X^1$, $X^2$, Y, Z, A, l, m and n have the same significance as defined above; B represents O, S, $CH_2$ or $NR^4$ ($R^4$ represents an alkyl group having 1 to 4 carbon atoms; and p and q represents an integer of 1 to 3.

That is, 0.8 to 1 molar amount of the compound represented by general formula (VI) is reacted with a aqueous formalin solution or paraformaldehyde in a solvent such as pentane, n-hexane, benzene, dichloromethane, chloroform, carbon tetrachloride, methanol, ethanol, propanol, tetrahydrofuran, dioxane, dimethylformamide, dimethylacetamide or a solvent mixture thereof, at a temperature of 0° C. to 100° C. for 10 to 50 hours in the presence of or absence of an acid such as hydrochloric acid or paratoluenesulfonic acid in a catalytic amount. Then, 0.1 to 1 molar amount of the compound represented by general formula (I-b) is added to the reaction mixture followed by reacting the mixture for further 10 to 50 hours at the same reaction temperature.

The compound represented by general formula (II) which is employed in the present invention may be prepared by the following process:

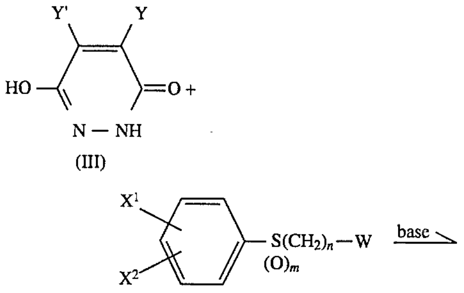

(III)

(IV)

-continued

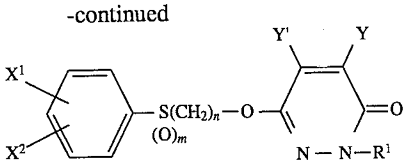

(II)

wherein $R^1$, $X^1$, $X^2$, Y, A, B, m and n have the same significance as defined above, and Y' represents a halogen atom, and W represents a halogen atom, a mesyloxy group and a tosyloxy group.

That is, the compound represented by general formula (III) is reacted with the compound shown by general formula (IV) in a solvent such as ether, dioxane, tetrahydrofuran, methyl ether, ethyl ether, dimethylformamide, dimethylacetamide, dimethylsulfoxide, hexamethylphosphoric triamide, etc. at a temperature of 0° C. to 150° C. for 3 to 24 hours in the presence of an equimolar or excess amount of an alkali metal salt such as sodium hydrogencarbonate, sodium carbonate, potassium carbonate, sodium hydroxide, potassium hydroxide, etc., an organic base such as triethylamine, diisopropylethylamine, pyridine, 4-dimethylaminopyridine, diazabicyclo-undecene, etc., sodium methoxide or sodium ethoxide. The compound represented by general formula (II) is thus obtained. The reaction proceeds in equimolar amounts of the reactants so that the compound shown by general formula (IV) may be used in an equimolar amount based on the compound shown by general formula (III). However, the compound of formula (IV) may also be used in an excess amount.

The compound of-formula (III) which is the starting material for preparing the compound shown by general formula (II) can be synthesized, e.g., by the process described in Angew. Chem. Internat. Edition, vol. 4, page 300 (1965); the compound of formula (IV) can be synthesized by the process described in, e.g., Org. Synth. III, 187 (1955).

Representative examples of the pyridazinone derivatives of the present invention are shown in Table 1 but the compounds of the present invention are not limited only thereto. In the table, Me, Et, $Q^1$ and $Q^2$ represent methyl, ethyl, morpholinomethyl and 4-methylpiperazin-1-ylmethyl, respectively.

TABLE 1

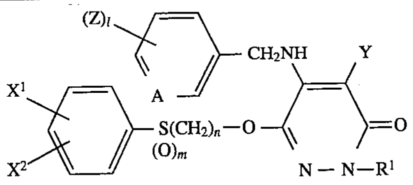

| No. | $X^1$ | $X^2$ | Y | (Z)l | A | $R^1$ | n | m | Melting point (°C.) |
|---|---|---|---|---|---|---|---|---|---|
| 1 | H | H | Cl | H | N | H | 2 | 0 | 184–185 |
| 2 | H | H | Cl | H | N | H | 3 | 0 | 152–155 |
| 3 | H | H | Br | H | N | H | 2 | 1 | 164–165 |
| 4 | H | H | Cl | 3,4-$(OMe)_2$ | CH | H | 2 | 0 | 119–120 |
| 5 | H | H | Cl | 3,4-$(OMe)_2$ | CH | H | 2 | 1 | 166–167 |
| 6 | H | H | Br | 3,4-$(OMe)_2$ | CH | H | 2 | 0 | 132–135 |
| 7 | H | H | Br | 3,4-$(OMe)_2$ | CH | H | 3 | 0 | 144–145 |
| 8 | H | H | Br | 3,4-$(OMe)_2$ | CH | H | 2 | 1 | 144–145 |
| 9 | H | H | Br | 3,4-$(OMe)_2$ | CH | H | 3 | 1 | 142–143 |
| 10 | H | H | Br | 3,4-$(OMe)_2$ | CH | H | 2 | 2 | 190–192 |
| 11 | H | H | Br | 3,4-$(OMe)_2$ | CH | H | 3 | 2 | 191–192 |
| 12 | H | H | Br | 3,4-$(OMe)_2$ | CH | $Q^1$ | 2 | 0 | 110–111 |
| 13 | H | H | Br | 3,4-$(OMe)_2$ | CH | $Q^1$ | 2 | 1 | 108–110 |
| 14 | H | 4-F | Br | 3,4-$(OMe)_2$ | CH | H | 2 | 0 | 146–148 |
| 15 | H | 4-F | Br | 3,4-$(OMe)_2$ | CH | H | 2 | 1 | 168–170 |
| 16 | H | 4-F | Br | 3,4-$(OMe)_2$ | CH | H | 2 | 2 | 218–220 |
| 17 | H | 4-F | Br | 3,4-$(OMe)_2$ | CH | $Q^2$ | 2 | 0 | 117–118 |
| 18 | H | 2-Cl | Br | 3,4-$(OMe)_2$ | CH | H | 2 | 0 | 144–145 |
| 19 | H | 2-Cl | Br | 3,4-$(OMe)_2$ | CH | H | 2 | 1 | 183–185 |
| 20 | H | 3-Cl | Br | 3,4-$(OMe)_2$ | CH | H | 2 | 0 | 176–177 |
| 21 | H | 3-Cl | Br | 3,4-$(OMe)_2$ | CH | H | 2 | 1 | 150–151 |
| 22 | H | 3-Cl | Br | 3,4-$(OMe)_2$ | CH | H | 2 | 2 | 194–195 |
| 23 | H | 4-Cl | Cl | H | N | H | 2 | 0 | 158–160 |
| 24 | H | 4-Cl | Cl | 3,4-$(OMe)_2$ | CH | H | 2 | 0 | 165–167 |
| 25 | 2-Cl | 6-Cl | Br | 3,4-$(OMe)_2$ | CH | H | 2 | 0 | 204–205 |
| 26 | 2-Cl | 6-Cl | Br | 3,4-$(OMe)_2$ | CH | H | 2 | 1 | 222–224 |
| 27 | H | 4-Me | Cl | H | N | H | 2 | 0 | 120–123 |
| 28 | H | 4-Me | Cl | 3,4-$(OMe)_2$ | CH | H | 2 | 0 | 112–113 |
| 29 | H | 4-Me | Cl | 3,4-$(OMe)_2$ | CH | H | 2 | 1 | 149–150 |
| 30 | H | 4-Me | Br | 3,4-$(OMe)_2$ | CH | H | 2 | 1 | 139–140 |
| 31 | 2-Me | 4-Me | Br | 3,4-$(OMe)_2$ | CH | H | 2 | 0 | 144–145 |
| 32 | 2-Me | 4-Me | Br | 3,4-$(OMe)_2$ | CH | H | 2 | 1 | 184–185 |
| 33 | 2-Me | 4-Me | Br | 3,4-$(OMe)_2$ | CH | H | 2 | 2 | 188–189 |
| 34 | H | 4-OMe | Cl | H | N | H | 2 | 0 | 98–99 |
| 35 | H | 4-OMe | Cl | 3,4-$(OMe)_2$ | CH | H | 2 | 0 | 115–117 |
| 36 | H | 4-OMe | Cl | 3,4-$(OMe)_2$ | CH | H | 2 | 2 | 173–175 |
| 37 | H | 4-CN | Br | 3,4-$(OMe)_2$ | CH | H | 2 | 0 | 214–215 |
| 38 | H | 4-CN | Br | 3,4-$(OMe)_2$ | CH | H | 2 | 1 | 183–185 |
| 39 | H | 4-$NO_2$ | Br | 3,4-$(OMe)_2$ | CH | H | 2 | 0 | 170–171 |

TABLE 1-continued

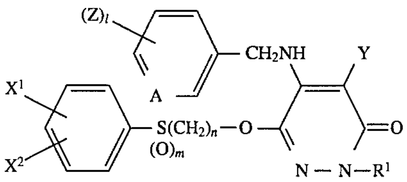

| No. | $X^1$ | $X^2$ | Y | (Z)l | A | $R^1$ | n | m | Melting point (°C.) |
|---|---|---|---|---|---|---|---|---|---|
| 40 | H | $4\text{-}NO_2$ | Br | $3,4\text{-}(OMe)_2$ | CH | H | 2 | 1 | 152–155 |
| 41 | H | 4-CONEt Et | Br | $3,4\text{-}(OMe)_2$ | CH | H | 2 | 0 | 148–150 |
| 42 | H | 4-CONEt Et | Br | $3,4\text{-}(OMe)_2$ | CH | H | 2 | 1 | 171–172 |

Herein after the compounds of the present invention and the starting compounds are described with reference to processes for preparing the same but the present invention is not deemed to be limited to these examples.

SYNTHESIS EXAMPLE

Synthesis of 4,5-dichloro-6-[3-(phenylthio)propyloxy]-3(2H)-pyridazinone (starting compound):

After 1.57 g of 1-bromo-3-phenylthiopropane, 2 g of 4,5-dichloro-6-hydroxy-3(2H)-pyridazinone and 1.3 g of triethylamine were dissolved in dimethylformamide, the mixture was stirred at room temperature for 24 hours. The reaction mixture was poured onto water. The formed crystals were taken by filtration and thoroughly washed with water. The crystals were recrystallized from ethanol to give 1.5 g of the objective compound. Yield, 52%, Melting point, 187°–188° C.

EXAMPLE 1

Synthesis of 4-chloro-6-[3-(phenylthio)propyloxy]-5-(3-picolylamino)-3(2H)-pyridazinone (Compound 2):

After 0.3 g of 4,5-dichloro-6-[3-(phenylthio)propyloxy]-3(2H)-pyridazinone and 0.243 g of 3-picolylamine were dissolved in a solvent mixture of water-dioxane (1:1), the mixture was heated to reflux for 8 hours. After completion of the reaction, the reaction mixture was poured onto water and extracted with ethyl acetate. After washing with water and drying, the solvent was distilled off. The resulting crystals were recrystallized from isopropanol to give 0.273 g of the objective compound. Yield, 73%, Melting point, 152°–155° C.

EXAMPLE 2

Synthesis of 4-bromo-5-(3,4-dimethoxyphenylmethylamino)-6-[2-(phenylsulfinyl)ethyloxy]-3(2H)-pyridazinone (Compound 8):

After 3.0 g of 4-bromo-5-(3,4-dimethoxyphenyl-methylamino)-6-[2-(phenylthio)ethyloxy]-3(2H)-pyridazinone was dissolved in 50 ml of dichloromethane, the solution was cooled to 0° C. Under ice cooling, 20 ml of a solution of 1.26 g of metaperchlorobenzoic acid in dichloromethane was added dropwise to the solution at 0° C. After completion of the dropwise addition, the mixture was stirred for 30 minutes at the same temperature and an excess of the peracid was decomposed by saturated aqueous sodium thiosulfate. The product was extracted with dichloromethane. After drying over magnesium sulfate, the solvent was distilled off. The resulting crude crystals were purified by silica gel column chromatography to give 2.3 g of the objective compound. Yield, 72%, Melting point, 144°–145° C.

EXAMPLE 3

Synthesis of 4-bromo-5-(3,4-dimethoxyphenylmethylamino)-6-[2-(phenylsulfonyl)ethyloxy]-3(2H)-pyridazinone (Compound 10):

After 0.4 g of 4-bromo-5-(3,4-dimethoxyphenylmethylamino)-6-[2-(phenylsulfonyl)ethyloxy]-3(2H)-pyridazinone and 0.35 g of metaperbenzoic acid were dissolved in dichloromethane, the solution was stirred for 7 hours at room temperature. Saturated aqueous sodium thiosulfate was added to the reaction solution to remove an excess of the peracid, followed extraction with dichloromethane. After drying over magnesium sulfate, the solvent was distilled off. The resulting crude crystals were thoroughly washed with ether and then with ethyl acetate to give 0.3 g of the objective compound. Yield, 72%, Melting point, 190°–192° C.

EXAMPLE 4

Synthesis of 4-bromo-5-(3,4-dimethoxyphenylmethylamino)-6-[2-(4-fluorophenylthio)ethyloxy]-2-(4-methylpiperazinylmethyl)-3(2H)-pyridazinone (Compound 17):

After 0.3 g of paraformaldehyde and 0.86 g of N-methylpiperazine were dissolved in 10 ml of dichloromethane, the solution was stirred at room temperature for 24 hours. Then, 0.51 g of 4-bromo-5-(3,4-dimethoxyphenylmethylamino)-6-[2-(4-fluorophenylthio)ethyloxy]-3(2H)-pyridazinone was added to the reaction mixture. The mixture was stirred for further 12 hours. The solvent was distilled off in vacuum to give 0.41 g of the objective compound. Yield, 69%, Melting point, 117°–118° C.

EXAMPLE 5

Synthesis of 4-bromo-5-(3,4-dimethoxyphenylmethylamino)-6-[2-(p-tolylsulfinyl)ethyloxy]-3(2H)-pyridazinone (Compound 30)

To a solution of 0.25 g of 4-bromo-5-(3,4-dimethoxyphenylmelthylamino)-6-[2-(p-tolylthio)ethyloxy]-3(2H)-pyridazinone in 20 ml of dichloromethane was added dropwise a solution of 0.11 g of metachloroperbenzoic acid in 5 ml of dichloromethane at 0° C. The resulting mixture was stirred for 30 minutes under the same condition. The excess reagent was decomposed by the addition of saturated aqueous sodium thiosulfate and the product was isolated by dichloromethane. The dichloromethane layer was washed with brine, dried over magnesium sulfate, and evaporated. The residue was purified over silicagel to give 0.18 g of the objective compound. Yield, 70%, Melting point, 139°–140° C.

EXAMPLE 6

Synthesis of 4-bromo-6-[2-(2-chlorophenylsulfinyl)ethyloxy]-5-(3,4-dimethoxyphenylmethylamino)-3(2H)-pyridazinone (Compound 19)

To a solution of 0.4 g of 4-bromo-6-[2-(2-chlorophenylthio)ethyloxy]-5-(3,4-dimethoxyphenylmethylamino)- 3(2H)-pyridazinone in 30 ml of dichloromethane was added dropwise a solution of 0.15 g of metachloroperbenzoic acid in 5 ml of dichloromethane at 0° C. The excess peracid was decomposed by the addition of saturated aqueous sodium thiosulfate. The mixture was diluted with dichloromethane, washed with brine, dried over magnesium sulfate and concentrated. The residue was chromatographed on silicagel to give 0.34 g of the objective compound. Yield, 83%, Melting point, 183°–185° C.

EXAMPLE 7

Synthesis of 4-bromo-5-(3,4-dimethoxyphenylmethylamino)-6-[2-(4-nitrophenylthio)ethyloxy]-3(2H)-pyridazinone (Compound 39)

1.5 g of 4,5-dibromo-6-[2-(4-nitrophenylthio)ethyloxy]-3(2H)-pyridazinone and 1.32 g of 3,4-dimethoxyphenylmethyl amine were disolved in water-dioxane (1:1) and refluxed for 7 hr. The reaction mixture was cooled to room temperature. The resulting crystals was collected by filtration and recrystallized from dioxane to give 1.1 g of the objective compound. Yield, 60%, Melting point, 170°–171° C.

EXAMPLE 8

Synthesis of 4-bromo-6-[2-(4-fluorophenylsulfonyl)ethyloxy]-5-(3,4-dimethoxyphenylmethylamino)-3(2H)-pyridazinone (Compound 16)

To a solution of 0.14 g of 4-bromo-6-[2-(4-fluorophenylthio)ethyloxy]-5-(3,4-dimethoxyphenylmethylamino)-3(2H)-pyridazinone in 40 ml of dichloromethane was added 0.33 g of metachloroperbenzoic acid in 10 ml of dichloromethane and the mixture was stirred at room temperature for 7 hr. After the decomposition of excess peracid with saturated aqueous sodium thiosulfate, the mixture was diluted with dichloromethane, washed with brine, dried and concentrated. The crude residue was purified by silicagel column chromatography to give 0.25 g of the objective compound. Yield, 69%, Melting point, 218°–220° C.

In case that the compounds of the present invention are employed as platelet aggregation inhibitors, the compounds may be administered orally or parenterally (intramuscularly, subcutaneously, intravenously). Since the compounds of the present invention are applicable in themselves as platelet aggregation inhibitors, the composition comprises the effective component generally in an amount of 0.01 to 100 wt %. Dose may vary depending upon condition, age, sex, body weight and form of application but in general, a daily dose for adult ranges from 0.1 to 1000 mg.

The compounds of the present invention can be prepared into pharmaceutical preparations such as powders, granules, tablets, sugar-coated tablets, capsules, pills, suspension, liquid, emulsion, ampoule, injection, isotonic solution, etc., in a conventional manner. Where solid preparations for oral administration are prepared by adding to the active ingredient and excipient, if necessary, a binder, a wetting agent, a disintegrator, a surfactant, a lubricant, a dispersing agent, a corrigent, a deodorant, a coloring agent, etc. and then preparing into tablets, coated tablets, granules, capsules, etc. in a conventional manner. Examples of the excipient used are lactose, glucose, sorbitol, corn starch and the like. Examples of the binder include polyvinyl alcohol, polyvinyl ether, ethyl cellulose, gum arabic, gelatin, hydroxypropyl cellulose, polyvinylpyrrolidone, etc. Examples of the disintegrator include calcium carbonate, calcium citrate, dextrin, etc. Examples of the lubricant are magnesium stearate, talc, polyethylene glycol, etc. Examples of the coloring agent are cacao powders, menthol, aromatic acids, peppermint oil, etc. These tablets and granules may be optionally coated with gelatin and other appropriate coating. Where injection is prepared, the active ingredient may be added, if necessary, with a pH controlling agent, a buffer, a surfactant, a dissolution aid, a solvent, a stabilizer, a preservative, etc., which is prepared into injection for subcutaneous, intramuscular or intravenous application.

Examples of pharmaceutical preparations are given below but the present invention is not deemed to be limited thereto. In the following, parts are all by weight.

Pharmaceutical Preparation 1:

| | |
|---|---|
| Compound of the present invention | 10 parts |
| Magnesium stearate | 10 parts |
| Lactose | 80 parts |

The above components are uniformly mixed and ground into powders or granulates to obtain powders.

Pharmaceutical Preparation 2:

| | |
|---|---|
| Compound of the present invention | 50 parts |
| Starch | 10 parts |
| Lactose | 15 parts |
| Ethyl cellulose | 20 parts |
| Polyvinyl alcohol | 5 parts |
| Water | 30 parts |

The above components are uniformly mixed, granulated and sieved to obtain granules.

Pharmaceutical Preparation 3

After 1 part of calcium stearate is added to 99 parts of the granules obtained in Pharmaceutical Preparation 3, the mixture is compression-molded to prepare a tablet having a diameter of 10 mm.

Pharmaceutical Preparation 4:

| | |
|---|---|
| Compound of the present invention | 95 parts |
| Polyvinyl alcohol | 5 parts |
| Water | 30 parts |

The above components are treated in a manner similar to Pharmaceutical Preparation 2 to obtain granules. After 10 parts of crystalline cellulose is added to 90 parts of the granules obtained, the mixture is compression-molded to prepare a tablet having a diameter of 8 mm. The tablet is prepared into a sugar-coated tablet, using an appropriate amount of a suspension mixture of syrup, gelatin and precipitated calcium carbonate and a coloring agent.

Pharmaceutical Preparation 5:

| | |
|---|---|
| Compound of the present invention | 0.5 parts |
| Nonionic surfactant | 2.5 parts |
| Physiological saline | 97 parts |

The above components are mixed while warming. The mixture is sterilized to give an injection.

Pharmaceutical Preparation 6:

The powders obtained in Pharmaceutical Preparation 1 is filled up in a commercially available capsule container to give a capsule.

In order to demonstrate the effects of the present invention, the following experiments were performed.

EXPERIMENT 1

Blood was collected from the ear vein of rabbit, together with 1/10 volume sodium citrate. Centrifugation at 1,200 rpm for 10 minutes gave the supernatant which was made platelet rich plasma (PRP). The blood was further centrifuged at 3,000 rpm for 10 minutes to give platelet poor plasma (PPP). The platelet count of PRP was adjusted to 300,000/μl with PPP, which was provided for the test. Platelet aggregation was determined with aggregometer (HEMATRACERVI, Niko Bioscience Co.) based on Born's turbidimetry. That is, 200 μl of PRP was charged in a cell and 1 μl of a drug solution dissolved in dimethylsulfoxide was added thereto. After incubation for 3 minutes, ADP was added in a concentration of 2 to 4 μM to cause aggregation. Change in transmittance in the cell was then monitored. The results are shown in Table 2, in terms of aggregation inhibition rate which was determined by comparing a transmittance of control with that obtained at the maximum aggregation on an aggregation curve when the transmittance of PRP was made 0% and the transmittance of PPP was made 100%.

TABLE 2

Aggregation Inhibition Rate (%)

| Compound No. | Dose $10^{-7}$ g/ml | Dose $10^{-6}$ g/ml |
|---|---|---|
| 1 | 37 | 100 |
| 2 | 27 | 100 |
| 4 | 100 | 100 |
| 6 | 100 | 100 |
| 7 | 74 | 100 |
| 8 | 82 | 100 |
| 10 | 100 | — |
| 11 | 71 | — |
| 12 | 100 | — |
| 13 | 100 | — |
| 14 | 100 | — |
| 15 | 100 | — |
| 16 | 100 | — |
| 17 | 100 | — |
| 18 | 100 | — |
| 19 | 100 | — |
| 20 | 90 | 100 |
| 23 | 100 | 100 |
| 24 | 100 | 100 |
| 27 | 80 | 100 |
| 28 | 100 | 100 |
| 29 | 100 | 100 |
| 30 | 100 | 100 |
| 31 | 100 | — |
| 32 | 100 | — |
| 33 | 100 | — |
| 34 | 64 | 100 |
| 35 | 83 | 100 |
| 36 | 83 | 100 |
| 37 | 100 | 100 |
| 38 | 100 | — |
| 39 | 93 | 100 |
| 41 | 100 | — |
| Comparative Compound A | 84 | 100 |
| Comparative Compound B | 79 | — |

For the purpose of comparison, compounds disclosed in International Patent Application No. WO91/16314 were examined.

Comparative Compound A:

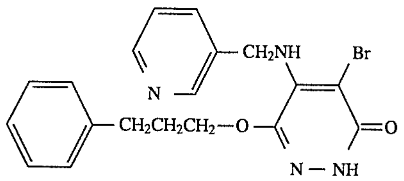

Comparative Compound B:

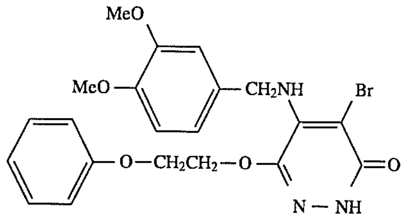

Experiment 2. Rabbit exo-vivo test

Japanese white rabbits weighing 3.0–4.0 kg were fasted for 18 hours. A drug suspension in 2% gum arabic aqueous solution was orally given to the animal in a definite dose. Blood was collected 1 and 4 hours after. PRP was prepared in a manner similar to Experiment 1 and ADP-inducing platelet aggregation function was determined. An inhibition rate was calculated based on an aggregation rate of ADP prior to administration of the compound.

TABLE 3

| Compound No. | Dose (mg/kg) | Average Inhibition Rate (%) 1 Hour | 4 Hours |
|---|---|---|---|
| 8 | 3 | 48 (3) | 23 (4) |
| | 30 | 72 (3) | 70 (4) |
| Comparative | 3 | 20 (3) | 23 (3) |
| Compound C | 30 | 36 (3) | 35 (3) |

( ) number of case

Comparative Compound C

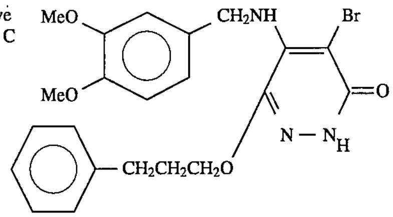

For the purpose of comparison, a compound disclosed in international Patent Application No. W091/16314 was examined.

EXPERIMENT 3

Activity of preventing thrombocytopenia in mice:

Collagen (Holm Co.) diluted with physiological saline was intravenously given through the vein to male ddY mice of 6 weeks old, weighing 28–31 g, which had been fasted for 4–5 hours, in a dose of 0.5 mg/kg. Five minutes after, blood was collected from the lower thigh vein under pentobarbital anesthesia through a plastic syringe treated with heparin containing 3.8% sodium citrate. The drug was orally given an hour before the collagen administration. The platelet count was measured with Sysmex E-4000. The inhibition activity is shown in terms of percentage of the platelet count when the platelet count of normal mouse was made 100 and the platelet count of control mouse was made 0.

TABLE 4

| Compound No. | Dose (mg/kg) | No. of case | Average Inhibition Rate (%) |
|---|---|---|---|
| 6 | 3.0 | 8 | 33.0** |
| 8 | 3.0 | 8 | 45.0*** |
| 12 | 3.0 | 8 | 43.0*** |
| 14 | 3.0 | 8 | 23.3** |
| 15 | 3.0 | 8 | 52.4*** |
| 16 | 3.0 | 8 | 35.7*** |
| 18 | 3.0 | 8 | 30.1*** |
| 19 | 3.0 | 8 | 33.8** |
| 37 | 3.0 | 8 | 35.4*** |
| 38 | 3.0 | 8 | 21.8* |
| 39 | 3.0 | 8 | 30.4** |
| 40 | 3.0 | 8 | 40.8*** |
| Comparative Compound C | 3.0 | 8 | 27.4 |

*: Statistically significant difference was noted with p = 5%
**: Statistically significant difference was noted with p = 1%
***: Statistically significant difference was noted with p = 0.1%

The pyridazinone derivatives of the present invention exhibit an inhibitory activity against platelet aggregation and are thus useful for the treatment of circulatory disorders such as myocardial infarction, pulmonary embolism, peripheral arterial embolism, cerebral thrombus, cerebral infarction, etc.

What is claimed is:

1. A pyridazinone compound represented by formula (I):

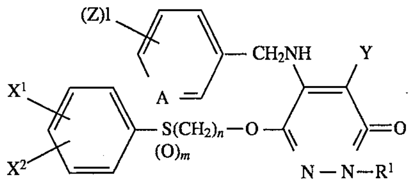

(I)

wherein $R^1$ represents a hydrogen atom; each of $X^1$ and $X^2$ independently represents a hydrogen atom, a halogen atom, an alkyl group having 1 to 6 carbon atoms, an alkoxy group having 1 to 6 carbon atoms, a cyano group, a nitro group or a group shown by $-CO-NR^2R^3$ (wherein each of $R^2$ and $R^3$ independently represents an alkyl group having 1 to 6 carbon atoms); Y represents a halogen atom; Z represents an alkoxy group having 1 to 6 carbon atoms; l represents 0 or an integer of 1 to 3; A represents CH; m represents 0 or an integer of 1 or 2; and n represents an integer of 1 to 8.

2. A pyridazinone compound according to claim 1, wherein $R^1$ is a hydrogen atom; $X^1$ is a hydrogen atom; $X^2$ is a hydrogen atom, a halogen atom, an alkyl group having 1 to 4 carbon atoms or an alkoxy group having 1 to 4 carbon atoms; Y is a halogen atom; Z is an alkoxy group having 1 to 4 carbon atoms; l is 0 or an integer of 1 to 3; A is CH; m is 0 or an integer of 1 to 2; n is 0 or an integer of 1 to 8.

3. A pyridazinone compound according to claim 1, wherein $R^1$ is a hydrogen atom, $X^1$ is a hydrogen atom, a halogen atom or an alkyl group having 1 to 4 carbon atoms; $X^2$ is a hydrogen atom or an alkyl group; Y is a bromo atom; z is an alkoxy group having 1 to 4 carbon atoms; l is 0 or an integer of 1 to 2; A is CH; m is 0 or an integer of 1 to 2; n is integer of 2 to 3.

4. A composition for inhibiting platelet aggregation comprising as an effective ingredient a pyridazinone compound represented by formula (I):

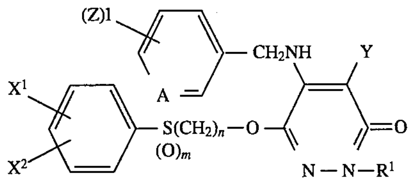

(I)

wherein $R^1$ represents a hydrogen atom; each of $X^1$ and $X^2$ independently represents a hydrogen atom, a halogen atom, an alkyl group having 1 to 6 carbon atoms, an alkoxy group having 1 to 6 carbon atoms, a cyano group, a nitro group or a group shown by $-CO-NR^2R^3$ (wherein each of $R^2$ and $R^3$ independently represents an alkyl group having 1 to 6 carbon atoms); Y represents a halogen atom; Z represents an alkoxy group having 1 to 6 carbon atoms; l represents 0 or an integer of 1 to 3; A represents CH; m represents 0 or an integer of 1 or 2; and n represents an integer of 1 to 8.

5. A composition for inhibiting platelet aggregation according to claim 4, wherein $R^1$ is a hydrogen atom; $X^1$ is a hydrogen atom; $X^2$ is a hydrogen atom, a halogen atom, an alkyl group having 1 to 4 carbon atoms or an alkoxy group having 1 to 4 carbon atoms; Y is a halogen atom; Z is an alkoxy group having 1 to 4 carbon atoms; l is 0 or an integer of 1 to 3; A is CH or N; m is 0 or an integer of 1 to 2; n is 0 or an integer of 1 to 8.

6. A composition for inhibiting platelet aggregation according to claim 4, wherein $R^1$ is a hydrogen atom, $X^1$ is a hydrogen atom, a halogen atom or an alkyl group having 1 to 4 carbon atoms; $X^2$ is a hydrogen atom or an alkyl group; Y is a bromo atom; Z is an alkoxy group having 1 to 4 carbon atoms; l is 0 or an integer of 1 to 2; A is CH; m is 0 or an integer of 1 to 2; n is integer of 2 to 3.

* * * * *